United States Patent
Hwang

(10) Patent No.: US 7,549,961 B1
(45) Date of Patent: Jun. 23, 2009

(54) SYSTEM AND METHOD SUPPORTING IMAGING AND MONITORING APPLICATIONS

(75) Inventor: Juinjet Hwang, Mercer Island, WA (US)

(73) Assignee: SonoSite, Inc., Bothell, WA (US)

( * ) Notice: Subject to any disclaimer, the term of this patent is extended or adjusted under 35 U.S.C. 154(b) by 445 days.

(21) Appl. No.: 10/903,848

(22) Filed: Jul. 30, 2004

Related U.S. Application Data

(60) Provisional application No. 60/491,919, filed on Jul. 31, 2003.

(51) Int. Cl.
*A61B 8/00* (2006.01)
*A61B 5/00* (2006.01)

(52) U.S. Cl. ..................... 600/440; 600/301

(58) Field of Classification Search .......... 600/437, 600/459, 301, 447; 128/661.01, 662.03
See application file for complete search history.

(56) References Cited

U.S. PATENT DOCUMENTS

| | | | |
|---|---|---|---|
| 5,295,485 A * | 3/1994 | Shinomura et al. ......... 600/443 |
| 5,722,412 A * | 3/1998 | Pflugrath et al. ............ 600/459 |
| 5,839,442 A * | 11/1998 | Chiang et al. ............... 600/447 |
| 5,882,300 A | 3/1999 | Malinouskas et al. |
| 6,113,547 A | 9/2000 | Catallo et al. |
| 6,120,447 A | 9/2000 | Mullen |
| 6,126,608 A * | 10/2000 | Kemme et al. .............. 600/459 |
| 6,142,946 A | 11/2000 | Hwang et al. |
| 6,238,344 B1 | 5/2001 | Gamelsky et al. |
| 6,241,673 B1 | 6/2001 | Williams |
| 6,440,072 B1 | 8/2002 | Schuman et al. |
| 6,475,146 B1 | 11/2002 | Frelburger et al. |
| 6,478,740 B2 | 11/2002 | Souney et al. |
| 6,481,887 B1 | 11/2002 | Mirabella |
| 6,540,679 B2 * | 4/2003 | Slayton et al. .............. 600/439 |
| 6,569,097 B1 * | 5/2003 | McMorrow et al. ......... 600/437 |
| 6,610,012 B2 * | 8/2003 | Mault ......................... 600/437 |
| 6,625,252 B2 | 9/2003 | Mirabella |
| 6,705,990 B1 | 3/2004 | Gallant et al. |
| 6,780,154 B2 * | 8/2004 | Hunt et al. .................. 600/446 |
| 7,038,588 B2 * | 5/2006 | Boone et al. ............. 340/573.1 |
| 7,095,442 B2 * | 8/2006 | van Zee ................. 348/333.01 |
| 7,115,093 B2 * | 10/2006 | Halmann et al. ............ 600/437 |
| 2002/0016545 A1 | 2/2002 | Quistgaard et al. |
| 2002/0040186 A1 | 4/2002 | Souney et al. |
| 2003/0097071 A1 | 5/2003 | Halmann et al. |
| 2004/0100376 A1 * | 5/2004 | Lye et al. ................ 340/539.12 |

FOREIGN PATENT DOCUMENTS

| | | |
|---|---|---|
| JP | 2002152314 | 5/2002 |
| WO | WO 00/70366 | 11/2000 |

\* cited by examiner

*Primary Examiner*—Eric F Winakur
*Assistant Examiner*—Michael T Rozanski
(74) *Attorney, Agent, or Firm*—Fulbright & Jaworski L.L.P.

(57) ABSTRACT

The present invention is directed to a system and method in which a portable medical device supports simultaneous imaging and monitoring applications. This portable device includes an external controller for receiving a PDA/MDA via a communication bus. An ultrasound scan head also is preferably attached to the external controller via an interconnect. In operation, real-time video feed of the patient may be acquired using the device and then displayed on the PDA/MDA. Using the ultrasound scan head in conjunction with the external controller, images may be acquired and displayed on the PDA/MDA, and vital sign monitoring of a single patient or multiple patients may be performed. Video feed, images and/or monitoring information may be transferred to a remote expert for review and analysis on the remote expert's communication device.

49 Claims, 11 Drawing Sheets

US 7,549,961 B1

SYSTEM AND METHOD SUPPORTING IMAGING AND MONITORING APPLICATIONS

CROSS-REFERENCE TO RELATED APPLICATION

The present application claims priority to U.S. Provisional Patent Application No. 60/491,919, entitled "Ultrasound Conversion Kit for a PDA/MDA," filed Jul. 31, 2003, the disclosure of which is hereby incorporated herein by reference.

TECHNICAL FIELD

Embodiments of this disclosure are directed to medical diagnostic and/or treatment systems and more particularly to medical devices for supporting imaging and monitoring applications.

BACKGROUND OF THE INVENTION

Clinical space at a hospital, such as a surgical suite, is typically crowded with various medical personnel and large pieces of equipment occupying the space. Many medical personnel may need to be present during the performance of a clinical procedure; however, routine monitoring or imaging examinations may only demand nurses or imaging technicians, such as sonographers, to be present to perform these examinations. While the physician in charge of the patient may not need to be present in the patient's room, the physician still will be interested in his/her patient's status with respect to these monitoring and/or imaging procedures. In some scenarios, the physician may have other matters to attend to around the hospital, but he/she still may need to advise the medical technician of additional procedures to be conducted or variations on the examination being conducted.

With respect to routine monitoring conducted in a hospital scenario, typically patients are attached to sensors that are used for the monitoring of vital signs. These sensors may be linked to a centralized center where medical personnel may monitor the patient's vital signs remotely. When a centralized center is employed, medical personnel are situated in this centralized center in order to monitor the progress of the patients. If, for example, a physician wants to monitor the patient's progress without entering a patient's room, he/she would need to be located in the centralized center. Accordingly, the physician or other medical personnel in charge of monitoring the patient must identify someone to monitor his/her patient when the physician needs to visit another patient's room or needs to be in a different area of the hospital.

Further, while the physician may monitor his/her patient's vital signs from the centralized center, when imaging procedures, such as ultrasound testing, are conducted, the physician would need to rely on a sonographer. Alternatively, the physician may need to enter the patient's room in order to be certain that the imaging is being performed correctly or to suggest variations on the imaging procedure being performed.

Accordingly, with respect to monitoring and imaging, a physician's movement is limited. The physician needs to either remain in the surgical suite or other location where the procedure or monitoring is being performed while these procedures are occurring or engage in limited monitoring in a centralized center.

In addition, the medical technician performing monitoring and/or imaging procedures within a clinical space demands a display for viewing the output from the monitoring of vital signs, for example, as well as for viewing the output from imaging using an ultrasound scan head. These external displays are typically bulky, taking up a large amount of space, and are generally not positioned close to one another. Thus, the medical technician is forced to shift his/her line of sight to view the displays while performing the imaging procedure, for example.

BRIEF SUMMARY OF THE INVENTION

The present invention is directed to systems and methods providing a portable diagnostic medical device that processes information from multiple sources. An embodiment of the invention is a unified device that supports dual-mode operation providing imaging and monitoring applications. The unified device preferably provides for imaging and the transfer of image information from one point to another. The unified device of embodiments also may preferably be used for patient monitoring, such as to monitor the patient's vital signs or other information about the patient. The unified device of embodiments is small, portable and suitable for mobile applications.

In an embodiment, a system includes an external controller for receiving a communication device, such as a Medical Data Assistant (MDA) or personal digital assistant (PDA), and a communication bus for mating with the communication device. This controller of embodiments preferably has a plurality of processors, including an image processor, scan conversion and video processor as well as a digital signal processor. The controller also includes means for communicating with an ultrasound scan head and/or sensors attached to a patient for monitoring purposes.

In additional or alternative embodiments, the external controller may be connected to a display for viewing purposes, whether local or remote and whether internal to a PDA/MDA or external thereto. Accordingly, a medical technician may view results from both monitoring and imaging applications on a single display on his/her communication device and simultaneously transmit these images to a remote expert in real-time for viewing and/or analysis of same.

Further embodiments of the present invention provide for the PDA/MDA to preferably use wireless technology, such as an infrared or RF communications link. This wireless link of embodiments provide for data or images to be transferred to various computer systems.

An embodiment of the invention provides a portable medical device having a sleeve for receiving a PDA/MDA wherein the PDA/MDA wirelessly receives monitoring information from a plurality of patients, as may be disposed in various clinical areas. When a medical technician needs to perform ultrasound imaging of a single patient, the medical technician, using the same amount of wireless bandwidth, may use the device for imaging, and then view the monitoring and/or imaging information on the PDA/MDA display.

In a further embodiment, a system and method are provided wherein a remote expert's display is wirelessly linked with a dual-mode device performing monitoring and/or imaging in a clinical space. Thus, the dual-mode device transmits to a remote expert's display such that the remote expert may view real-time data and/or images of the patient being examined remotely. The remote expert also may view images and/or processed signals acquired in the clinical space and transmitted using the dual-mode device.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
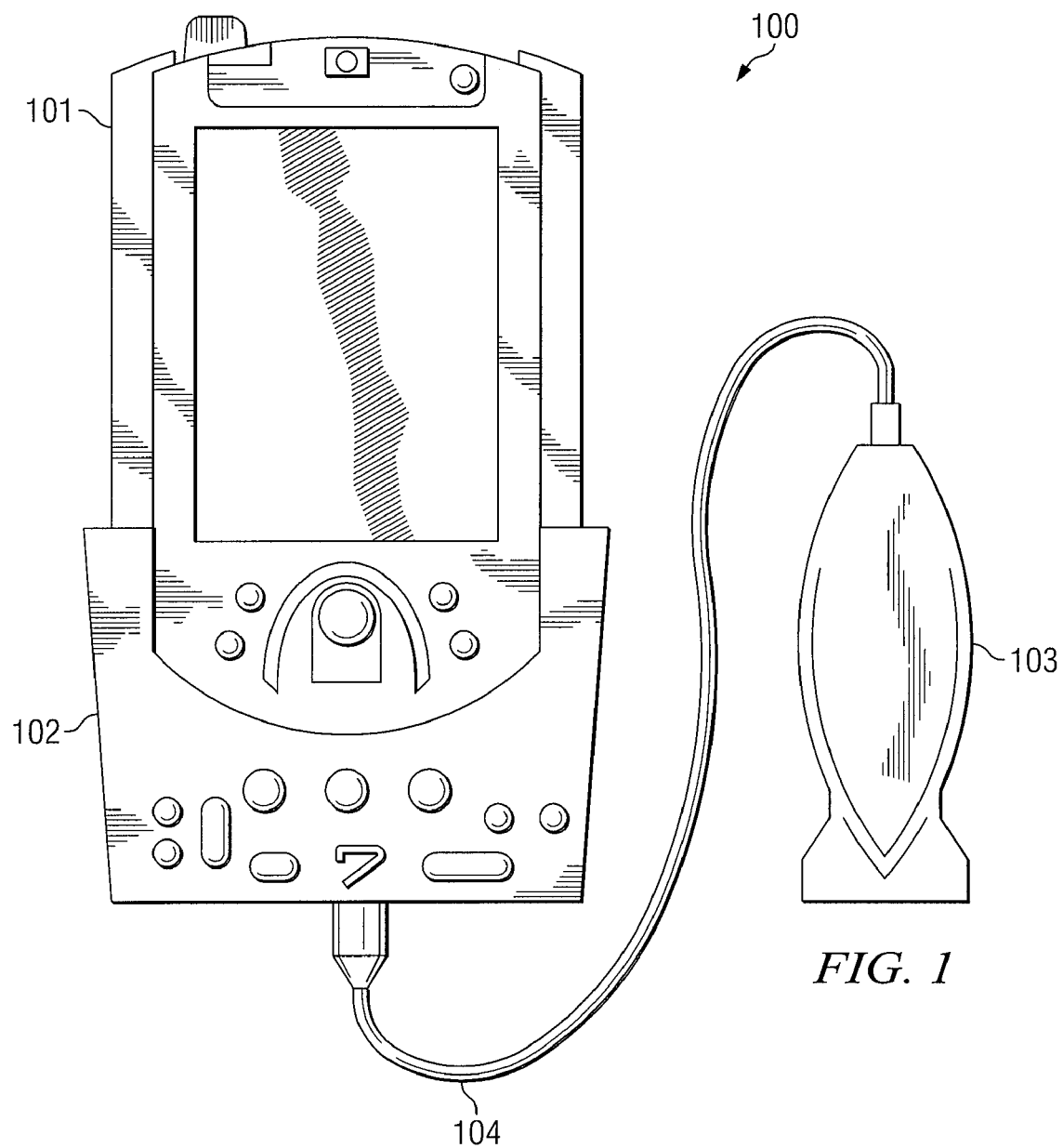
FIG. 1 depicts an embodiment of a unified device for performing monitoring and imaging functions.

In a first embodiment, a unified device for processing information, such as monitoring and imaging, from multiple sources is provided. The device is comprised of an external controller or sleeve for receiving a personal digital assistant (PDA) or medical data assistant (MDA), and an interconnect to allow the external controller and/or PDA/MDA to communicate with an ultrasound scan head. FIG. 1 depicts an embodiment of dual monitoring/imaging device 100 comprising PDA/MDA 101, external controller 102 for receiving PDA/MDA 101, scan head 103, and interconnect 104 for attaching scan head 103 to external controller 102. Interconnect 104, which may be wireless or wireline, allows for communication between scan head 103 and external controller 102 as well as to allow communication of ultrasound signals generated by scan head 103 to external controller 102. External controller 102 processes the signals into images for eventual display on PDA/MDA 101 and/or external display systems (not shown). Each of these components of device 100 will be described in more detail below with respect to FIG. 2.

Figure 2A:
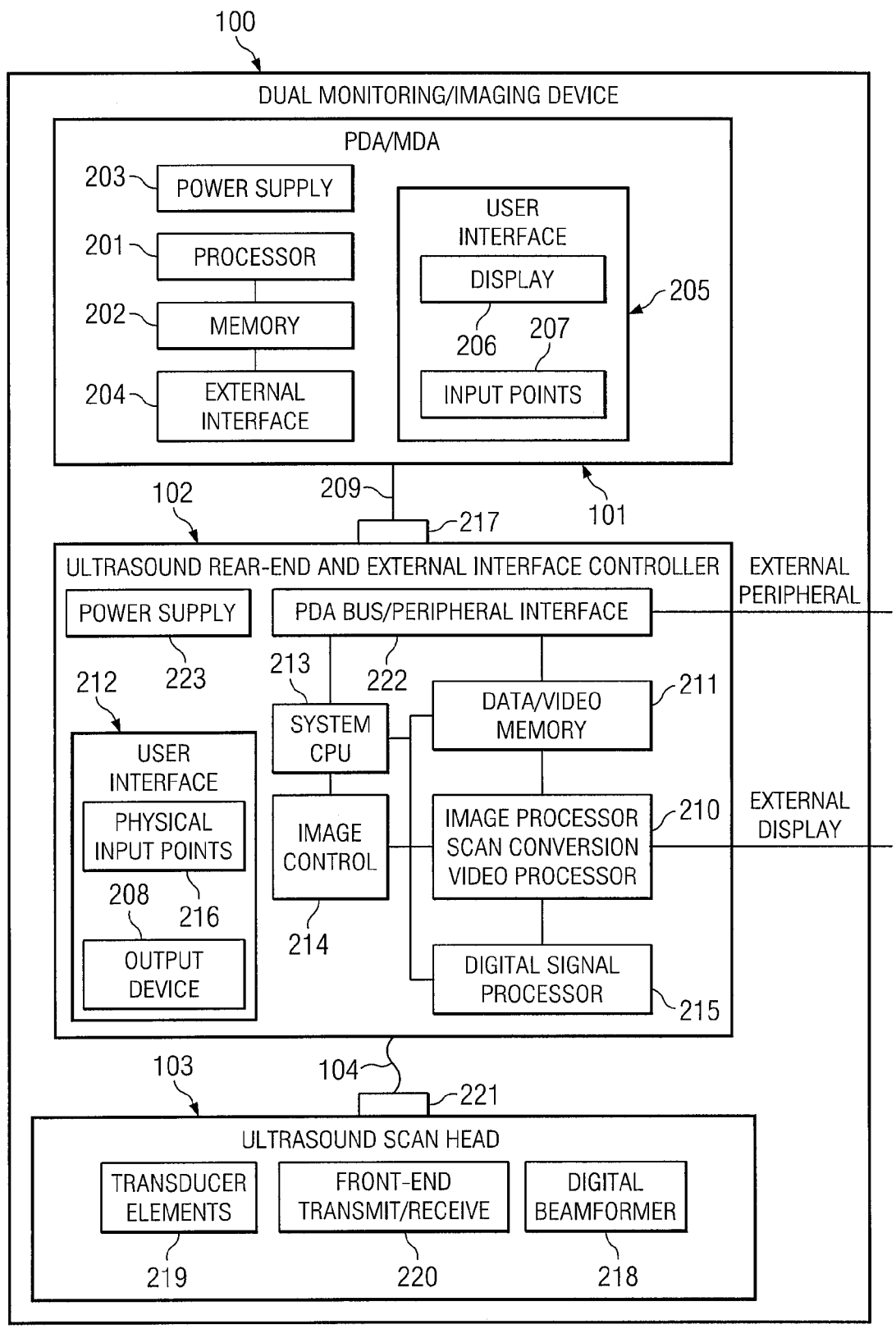
FIG. 2A depicts a block diagram illustrating an embodiment of the device of FIG. 1 using the PDA/MDA as a peripheral.

FIGS. 2A-2F depict block diagrams of various embodiments of the device of FIG. 1. FIG. 2A depicts a block diagram where PDA/MDA 101 is used as a peripheral for dual monitoring/imaging device 100. PDA/MDA 101 is comprised of processor 201, memory 202, power supply 203, external interface 204, and user interface 205 including display 206 and input points 207. Processor 201 may be a general purpose CPU or may be a low power/mobile specific processor, for example. Processor 201 is coupled to memory 202. Memory 202 includes storage for program code as well as storage for operation of device 100. External interface 204, as shown in FIG. 2A, is coupled to memory 202, wherein external interface 204 is preferably controlled by software stored in memory 202. However, in another embodiment, external interface may be coupled to processor 201 or alternatively, operate independently of processor 201. External interface 204 preferably provides connectivity of PDA/MDA 101 with other computer systems, such as those systems for monitoring using sensors attached to patients. Further embodiments provide for PDA/MDA 101 to communicate with a remote expert's communication device or other display for viewing results obtained by device 100, as will be described in more detail with respect to FIGS. 4 and 5. External interface 204 (e.g., a built-in IR interface or a wireless network adapter) preferably uses wireless technology, such as an infrared or RF communications link. Accordingly, data and images being displayed on PDA/MDA 101 may be transferred to various systems. Although this embodiment is described with respect to use of a wireless link, external interface 204 of PDA/MDA 101 may take any suitable form, although some loss of mobility may result.

PDA/MDA 101 preferably provides wireless connectivity in order to send an ultrasound image or a video image back to a remote expert's communication device or display screen in order to analyze the images and provide suggestions or direction about how to proceed with the monitoring or imaging being performed as will be discussed in more detail with respect to FIGS. 3A-3D.

Communication link 209 preferably couples PDA/MDA 101 to external controller 102. Accordingly, data transfer and manipulation of data received from patient monitoring and/or imaging procedures occurs via communication link 209 (e.g., an expansion adapter of PDA/MDA), according to embodiments of the invention.

User interface 205 includes hardware and software components such that a user may interface with PDA/MDA 101 to monitor a patient's vital signs as well as to direct operation of ultrasound scan head 103 which may be attached to external controller 102 via interconnect 104. User interface 205 includes physical input points 207, which may comprise, but are not limited to, a keyboard, joystick, mouse pad, touch screen, and function buttons. Accordingly, using user interface 205, a user may adjust what images or data is being output on display 206 as well as adjust the rate of display of images and/or video feed being sent to PDA/MDA 101 and/or to a remote expert's display.

User interface 205 includes output device or display 206, such as a color, grayscale or black and white display screen. This screen preferably displays images in a variety of formats, allowing for simultaneous display of monitoring and imaging outputs, as will be discussed in more detail with respect to FIGS. 3A-3D.

Depending on the type of PDA/MDA in communication with external controller 102, space may be available for specialized circuitry specifically adapted for ultrasound signal processing such that a controller or portions thereof may be embedded into the PDA/MDA. This preferably permits scan head 103 to be directly connected to a port on the PDA/MDA using a thin wire connector. A thin wire connector is preferably a pair of Low Voltage Differentiating Signal (LVDS) lines and is preferably used when beamforming is to be performed in the scan head as opposed to the external controller. Alternatively, a universal serial bus (USB), a USB2 or an IEEE1394-type interface, or other suitable interface, may be used. Alternative embodiments provide for using a PDA/MDA wireless interface, such as an infrared (IR) port or radio frequency (RF), such as Bluetooth or wireless LAN, to communicate directly, for example, to a corresponding IR port which may be built into the scan head.

Ultrasound rear-end and external interface controller 102 is provided for releasably engaging PDA/MDA 101 via output device 217 attached to PDA/MDA 101 through communication link 209. This external controller may take the form of a sleeve or another form of docking station for the PDA/MDA. External controller 102 releasably receives ultrasound scan head 103 via interconnect 104, which may be a wireless or a wireline connection. Further, the attachment of scan head 103 to external controller 102 may be releasable.

External controller 102 of the illustrated embodiment includes digital signal processor 215, image processor/scan conversion/video processor 210, data/video memory 211, system CPU 213, image control 214, PDA bus/peripheral interface 222, power supply 223, and user interface 212 including physical input points 216 and output device 208. Ultrasound scan head 103 transmits signals to external controller 102. Digital signal processor 215 filters the signals and transmits the filtered signals to image processor/scan conversion/video processor 210 for scan conversion and the production of signals, such as video signals. Digital signal processor 215 may transmit the received signals to data/video memory 211 for storage, or alternatively, signals are sent to data/video memory 211 for storage after processing at processor 210. Images and/or video also may be sent to an external display directly from processor 210 as shown by the line extending to the right of processor 210. In another embodiment, PDA bus/peripheral interface 222 is provided wherein memory 211 is coupled to interface 222, and data/video stored in memory 211 may be transmitted to an external peripheral via interface 222. Further, system CPU 213 manages all ultrasound data acquisition events and sends commands to scan head 103 for mode switching, selection of filters and aperture control. Dedicated image control circuits are implemented in image control 214 to provide timing and to control signals for triggering transmit/receive, channel multiplexing, A/D conversion, and beamform processing. Power supply 223 also is provided in external controller 102 so that device 100 may be operated without connecting to a power source separate from the device.

Similar to user interface 205 of PDA/MDA 101, user interface 212 includes physical input points 216 for user manipulation of the signals to be collected by ultrasound scan head 103 and then processed for display on PDA/MDA 101. Accordingly, if the user prefers a faster rate of ultrasound image acquisition, the user may, for example, press a button on external controller 102 in order to alter the rate. Alternative embodiments provide physical input points 216 on external controller 102, such as TGC gain, depth and focus controls, in order to manipulate image acquisition and processing of acquired images. User interface 212 also may include output device 208 (e.g., LCD or audio) on external controller 102, or alternatively, external controller 102 outputs information on display 206 of PDA/MDA 101.

In another embodiment, an external add on card may preferably be used as the external controller. This embodiment allows for construction of, for example, a specialized PCMCIA card having signal processing components within the card. The card then may be preferably inserted into a receiving PCMCIA slot, such as PDA bus/peripheral interface 222, in order to operate on the internal power of device 100. The card then may operate as the external controller for scan head 103.

A user may selectively engage and disengage PDA/MDA 101 and external controller 102. When a user elects to detach PDA/MDA 101 from external controller 102, PDA/MDA 101 may be disconnected from external controller 102 by releasing communication link 209. When PDA/MDA 101 has been disengaged, the user may attach a different unit to external controller 102 as appropriate. For example, another unit may have a different type of image processing capability, such as image processing module 105, to provide additional processing power for ultrasound image quality enhancement, as will be discussed with respect to FIG. 2B.

In a further embodiment, when detached from external controller 102, PDA/MDA 101 preferably may still be wirelessly connected to external controller 102 via external interface 204. As an example, PDA/MDA 101 may still receive processed signals from external controller 102; however, PDA/MDA 101 may be inserted into a cart-style assembly having a better quality or larger display screen in order to provide for improved analysis of ultrasound images processed by external controller 102. Alternatively, PDA/MDA 101 may remain physically connected to external controller 102, and then PDA/MDA 101 may preferably transfer images received from external controller 102 to another computer system having a larger or better quality display screen.

Additional embodiments provide that if PDA/MDA 101 is unavailable or the medical technician desires a larger screen for display, external controller 102 may preferably support an external monitor which may be connected to external controller via image processor 210, for example. Alternatively, external controller 102 includes port 217, such as a video port, for receiving communication link 209. Although communication link 209 has been described previously with respect to engaging PDA/MDA 101, communication link 209 may also engage this external video monitor. Video port 217 of external controller 102 may comprise a super VGA port, for example, such that the external controller may be attached to a larger monitor for display purposes. Alternatively, this video port of external controller 102 may be connected to a head mount display. Although a monitor and a head mount display have been described as external monitoring devices, the video port of external controller 102 may be attached to any display device that the user desires to utilize for viewing the acquired ultrasound images, including, but not limited to a television, computer screen, projection screen, and a cart-type ultrasound system having a display.

Although PDA/MDA 101 is preferably attached to external controller 102 through communication link 209, there may be occasions when the connectivity of PDA/MDA 101 to external controller 102 may not be needed. In alternative embodiments, the user may not require the PC functionality provided by PDA/MDA 101. Accordingly, external controller 102 preferably may serve as a complete ultrasound system, such that the external controller does not need to be connected to a PDA/MDA. In this embodiment, output 208 of user interface 212 provides means for displaying signals obtained from scan head 103 or other monitoring or imaging information.

While a user sometimes may not need the PC functionality of PDA/MDA 101, it should be appreciated, however, that PDA/MDA 101 may be releasably attached to external controller 102 out of convenience to the medical technician or user. Typically PDAs/MDAs provide for a number of applications that may be of use to the medical technician in the course of a medical procedure, including but not limited to scheduling, note-taking, and data storage and other data retrieval functions. Accordingly, PDA/MDA 101 contains a variety of applications that stand apart from external controller 102. However, when PDA/MDA 101 is connected to the external controller, PDA/MDA 101 preferably adds this functionality to external controller 102.

Ultrasound scan head 103 of FIG. 2A is preferably attached to external controller 102 via interconnect 104 in order to perform ultrasound imaging and then transfer signals to external controller 102. Scan head 103 preferably is a transducer array for its solid state, electronic control capabilities, variable aperture, image performance and reliability. This array may be, but is not limited to, a linear array, a curved linear array, or a phased array. Various acoustic lenses may be used in conjunction with scan head 103, including lenses shaped and spatially cut to simulate a linear array, for example, without the need for an electronic controller.

Scan head 103 includes transducer elements 219, front-end/transmit-receive circuit 220 and digital beamformer 218. Transducer elements 219 acquire echoes. Transmit-receive circuit 220 preferably switches aperture, multiplexes receive channels, sends transmit pulses, receives and digitizes echoes acquired from transducer elements 219. The digitized data from receive channels are then preferably delayed and integrated in digital beamformer 218. Control logics and timing circuits for aperture control and dynamic focusing are preferably included in digital beamformer 218. The beamformed data are then transmitted from scan head 103 to external controller 102 for further processing and eventual display, as has been described above. Scan head 103 may be capable of various ultrasound scan modes, including but not limited to M-Mode, B-Mode, Doppler, and 3D. Scan head 103 also preferably includes port 221 for attaching scan head 103 to external controller 102 via interconnect 104.

The ultrasound scan head typically weighs less than six ounces (6 oz, or 170.25 g). The weight of the scan head includes interconnect 104 for communicating with external controller 102, such as a thin cable connector. However, scan head 103 may weigh as much as 10 ounces when these elements are combined.

In a further embodiment, scan head 103 may include an ergonomic grip. This ergonomic grip make it easier for a user to handle and operate scan head 103 while also manipulating external controller 102.

Another embodiment provides for scan head 103 to preferably include an external hook or clip. Thus, the user may clip ultrasound scan head 103 to his/her clothing or another article, such as the patient's bed, when scan head 103 is not in use.

Interconnect 104 from external controller 102 to ultrasound scan head 103 preferably may be wired or wireless. In a hardwire mode, a thin wire cable or an optical fiber link may be used. When interconnect 104 of embodiments is wired, the interconnect may be a thin wire or a wide broadband serial interface. In another embodiment, interconnect 104 may be a general, low voltage differential signaling cable. Further embodiments may provide for an interconnect that may include, but is not limited to, USB, broadband, or high speed USB. High speed USB includes the broadband 1394 as well as other wide media networks available for some other applications. In a wireless configuration, an IR or RF signal may be used. Other wireless interconnect options also are available including, but not limited to, ultra wide band (UWB), wireless USB, and UWB wireless 1394. Accordingly, as wireless options develop, it may be possible to substitute wired options with other wireless options. Although interconnect 104 has been described with respect to hardwire and wireless configurations, this does not limit the means for communication available.

In operation with external controller 102, PDA/MDA 101 electrically couples to external controller 102 via communication link 209. This coupling allows for data transfer and manipulation of data received from patient monitoring and imaging procedures performed by external controller 102. Thus, PDA/MDA 101 may communicate with external controller 102 as well as other hardware/software associated with external controller 102, such as ultrasound scan head 103 or sensors attached to patients for monitoring, using communication link 209 or through PCMCIA bus/peripheral interface 222.

Figure 2B:
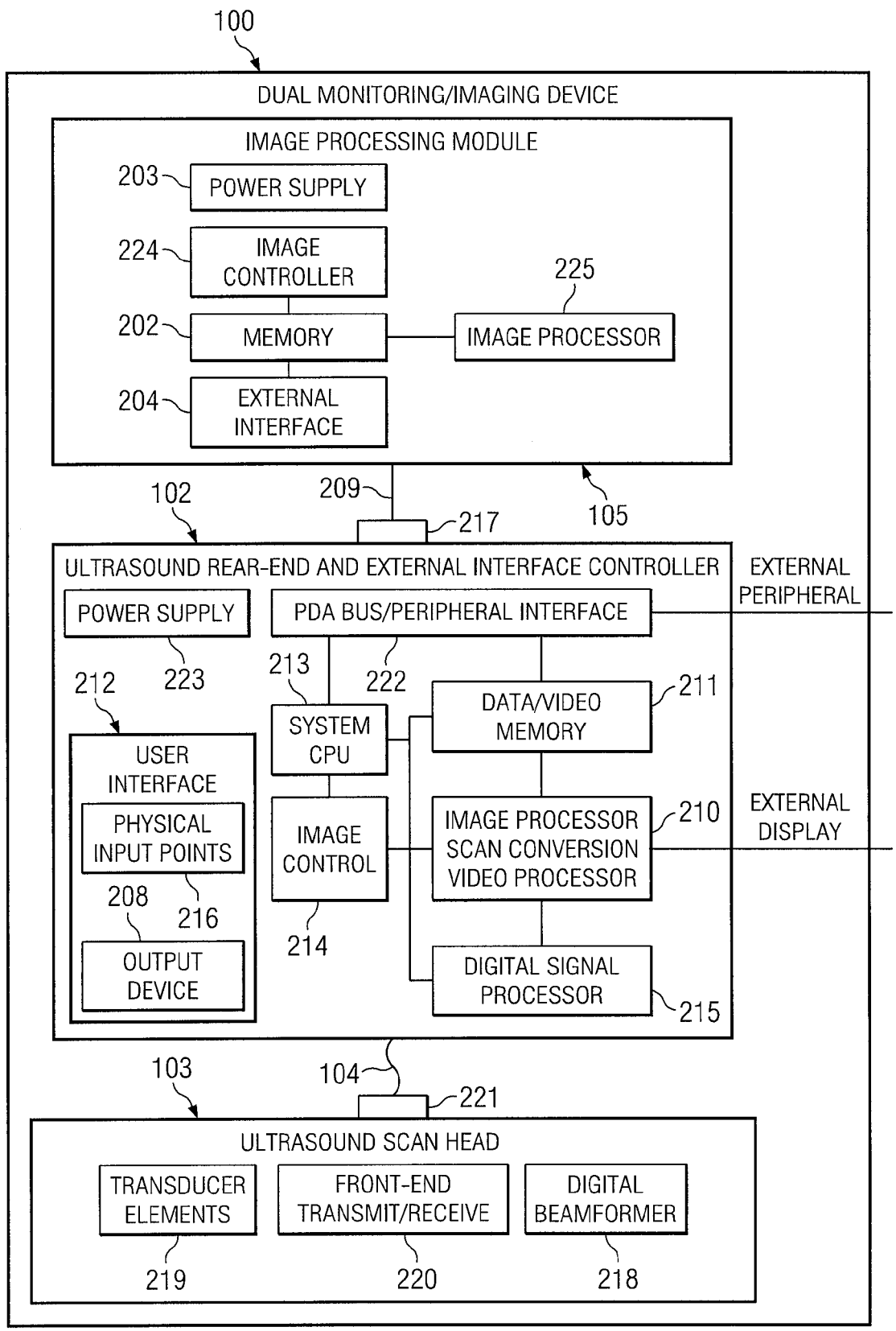
FIG. 2B depicts a block diagram illustrating an embodiment of the device of FIG. 1 using an image processing module as a peripheral.

Turning to FIG. 2B, FIG. 2B depicts a block diagram wherein external controller 102 receives image processing module 105 in place of PDA/MDA 101. Image processing module 105 preferably may be employed when a user desires enhanced video processing features beyond what is offered by external controller 102. Image processing module 105, like PDA/MDA 101 described in FIG. 2A, includes power supply 203, memory 202 and external interface 204; however, image processing module 105 includes image controller 224 which is coupled to memory 202, and image processor 225 which also is coupled to memory 202. Similar to FIG. 2A, external controller 102 communicates with image processing module 105 via communication link 209.

Although PDA/MDA 101 is replaced by image processing module 105 in FIG. 2B, it should be appreciated that external controller 102 and scan head 103 preferably include the same components as have been described with respect to FIG. 2A.

Figure 2C:
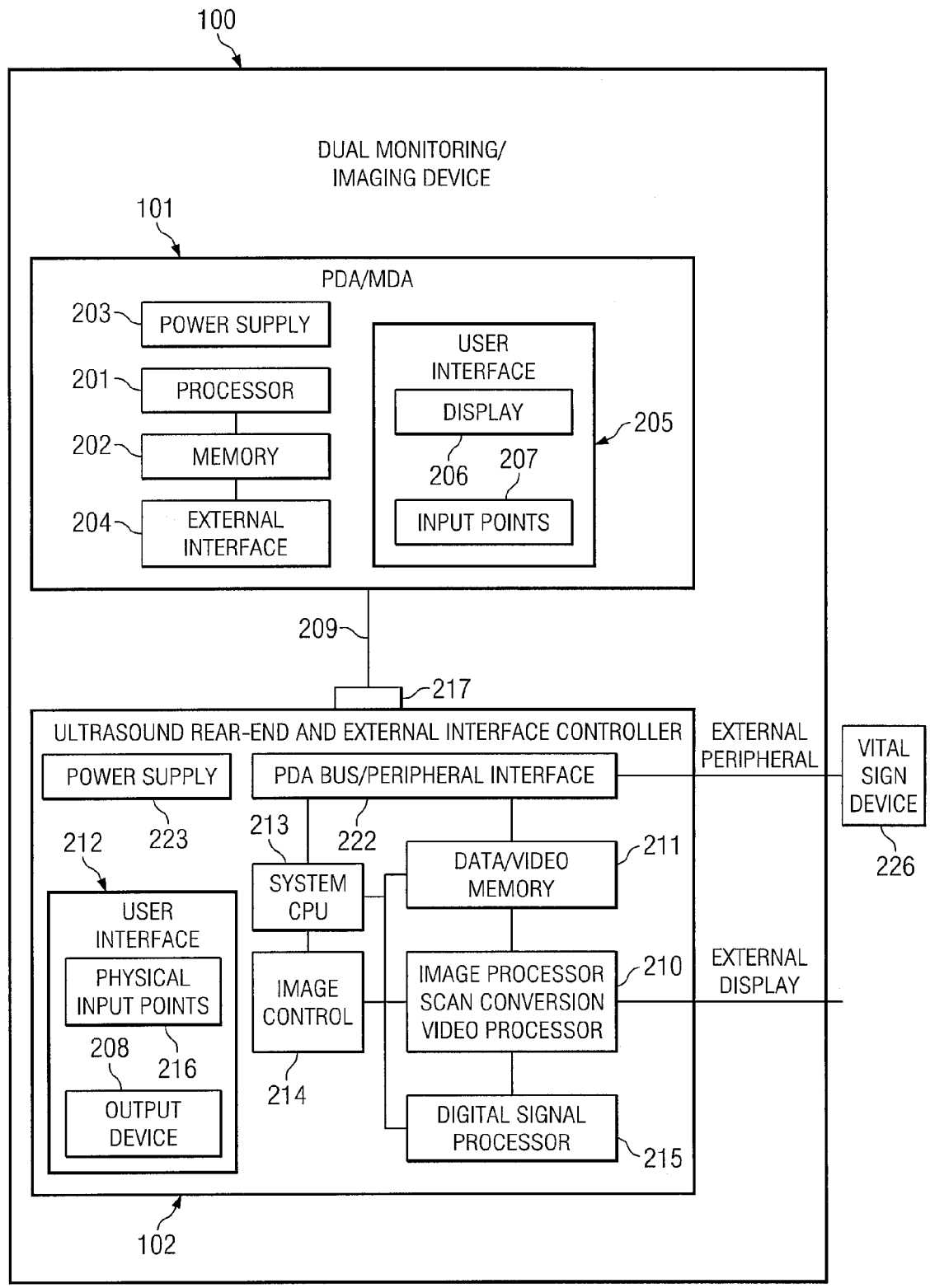
FIG. 2C depicts a block diagram illustrating an embodiment of the device of FIG. 1 for vital sign monitoring.

FIG. 2C depicts an embodiment of the present invention for use in the monitoring of a patient's vital signs. In the illustrated embodiment, external controller 102 is not in communication with scan head 103. Rather, external controller 102 is placed in communication with vital sign device 226. When scan head 103 is removed, device 100 serves as a display system interfaced with PDA/MDA 101 wherein vital sign device 226 is connected to external controller 102 via a wired or wireless connection. It should be appreciated that the components of PDA/MDA 101 and external controller 102, as shown in FIG. 2C, have been previously described with respect to FIG. 2A.

Software may be loaded into PDA/MDA 101 that is capable of displaying information about the patient that the medical technician is collecting. For example, vital sign device 226 may be a portable EKG system designed for monitoring using PDA/MDA 101. When the portable EKG system is linked to one particular patient for monitoring, the data collected on the portable EKG may be transferred to PDA/MDA 101 via external interface 204 or PDA bus/peripheral interface 222. While PDA/MDA 101 monitors a patient's vital signs, ultrasound scan head 103 may simultaneously acquire ultrasound imaging data and transfer this data from scan head 103 to external controller 102 via interconnect 104 for display on PDA/MDA 101. In alternative embodiments, PDA/MDA 101 may be detached from external controller 102, and communication between external controller 102 and PDA/MDA 101 may preferably be accomplished via external interface 209 over a wireless link, for example.

Figure 2D:
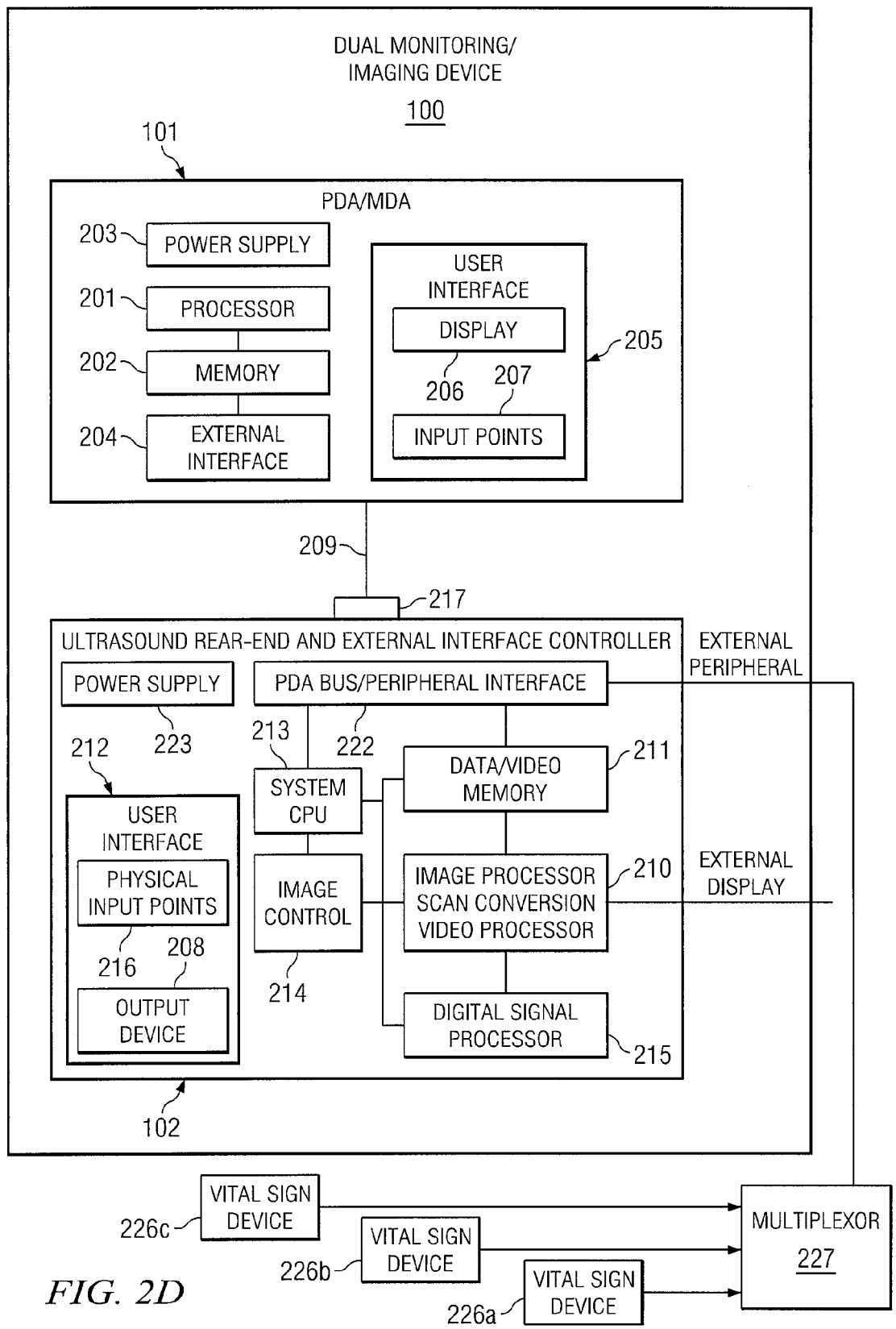
FIG. 2D depicts a block diagram illustrating an embodiment of the device of FIG. 1 in operation with a multiplexor for monitoring multiple vital signs.

FIG. 2D depicts a block diagram of a scenario wherein the user of device 100 may perform vital sign monitoring of more than one signal type from the same patient or of a single signal type from more than one patient. As shown in FIG. 2D, PDA bus/peripheral interface 222 of external controller 102 is in communication with multiplexor 227. Multiplexor 227 communicates with more than one vital sign device, 226a, 226b, 226c. Accordingly, vital signs are preferably collected by vital sign devices 226a, 226b, 226c, and the signals acquired by each may be multiplexed for transfer to external controller 102 and eventual display on PDA/MDA 101. Communication between multiplexor 227 and vital devices 226a, 226b, 226c may be via wireline or wireless radio.

As an example, while performing rounds in a clinical space, a physician may carry device 100 and receive monitoring information for multiple patients at the same time. The physician then may switch device 100 into ultrasound imaging mode in order to collect an image. After conducting the imaging procedure, the physician may then switch back to receive patient monitoring information. Alternatively, a physician may collect monitoring information and then perform ultrasound imaging in order to send to a remote expert, as will be discussed in more detail with respect to FIGS. 4 and 5.

Figure 2E:
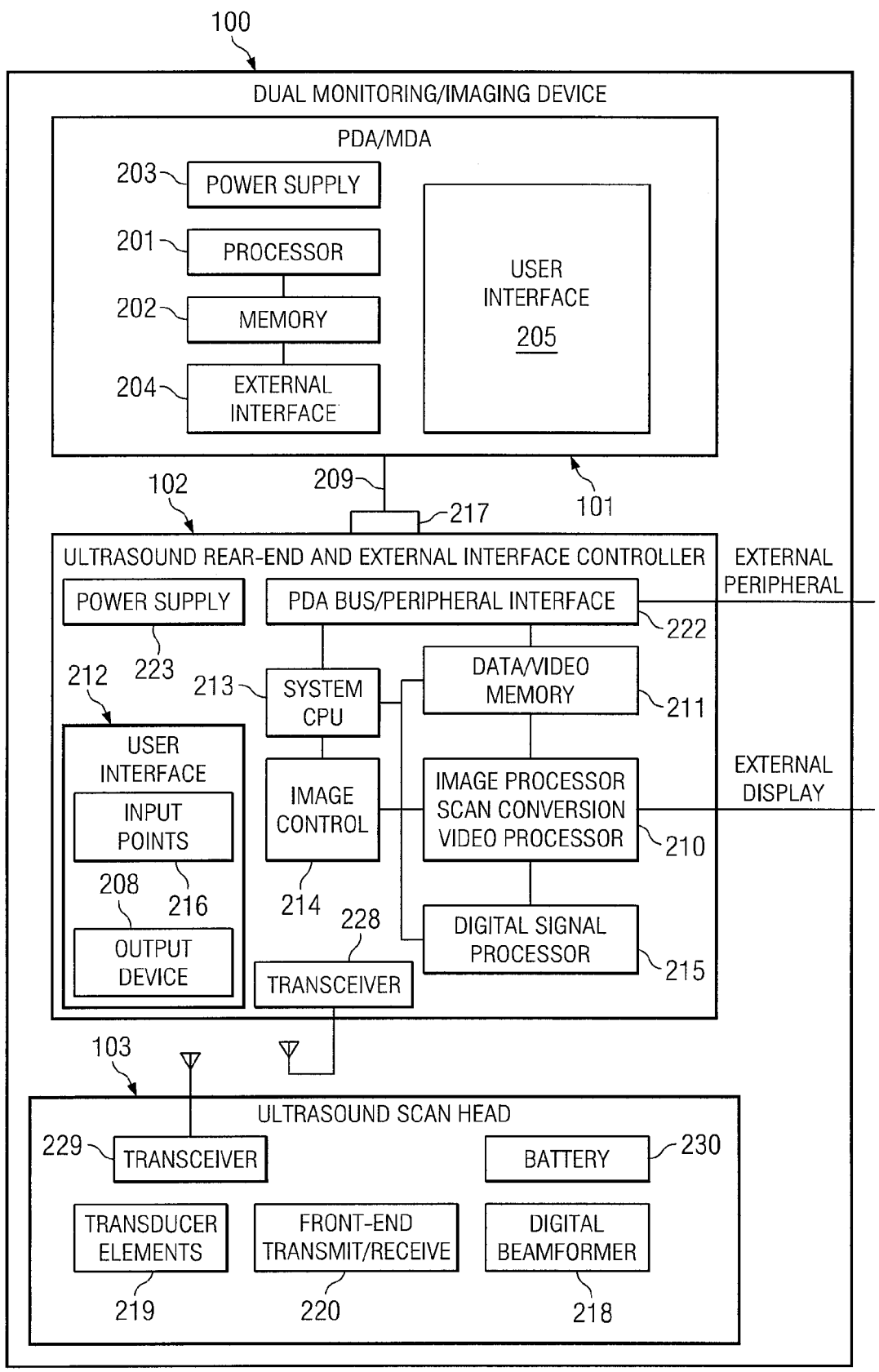
FIG. 2E depicts a block diagram illustrating an embodiment of the device of FIG. 1 wherein a scan head communicates with an external controller wirelessly.

Illustrated in FIG. 2E is an embodiment wherein PDA/MDA 101 and external controller 102 connected by communication link 209 communicate with scan head 103 via a wireless connection. As shown in FIG. 2E, external controller 102 includes transceiver 228, and scan head 103 includes transceiver 229. Transceiver 228 and transceiver 229 communicate with one another. Accordingly, scan head 103 may be used in a position remote from external controller 102 and PDA/MDA 101 while remaining in communication with each. As scan head 103 operates independently from external controller 102 in FIG. 2E, it should be appreciated that scan head 103 preferably includes battery 230 in order to maintain sufficient power to complete image acquisition.

Figure 2F:
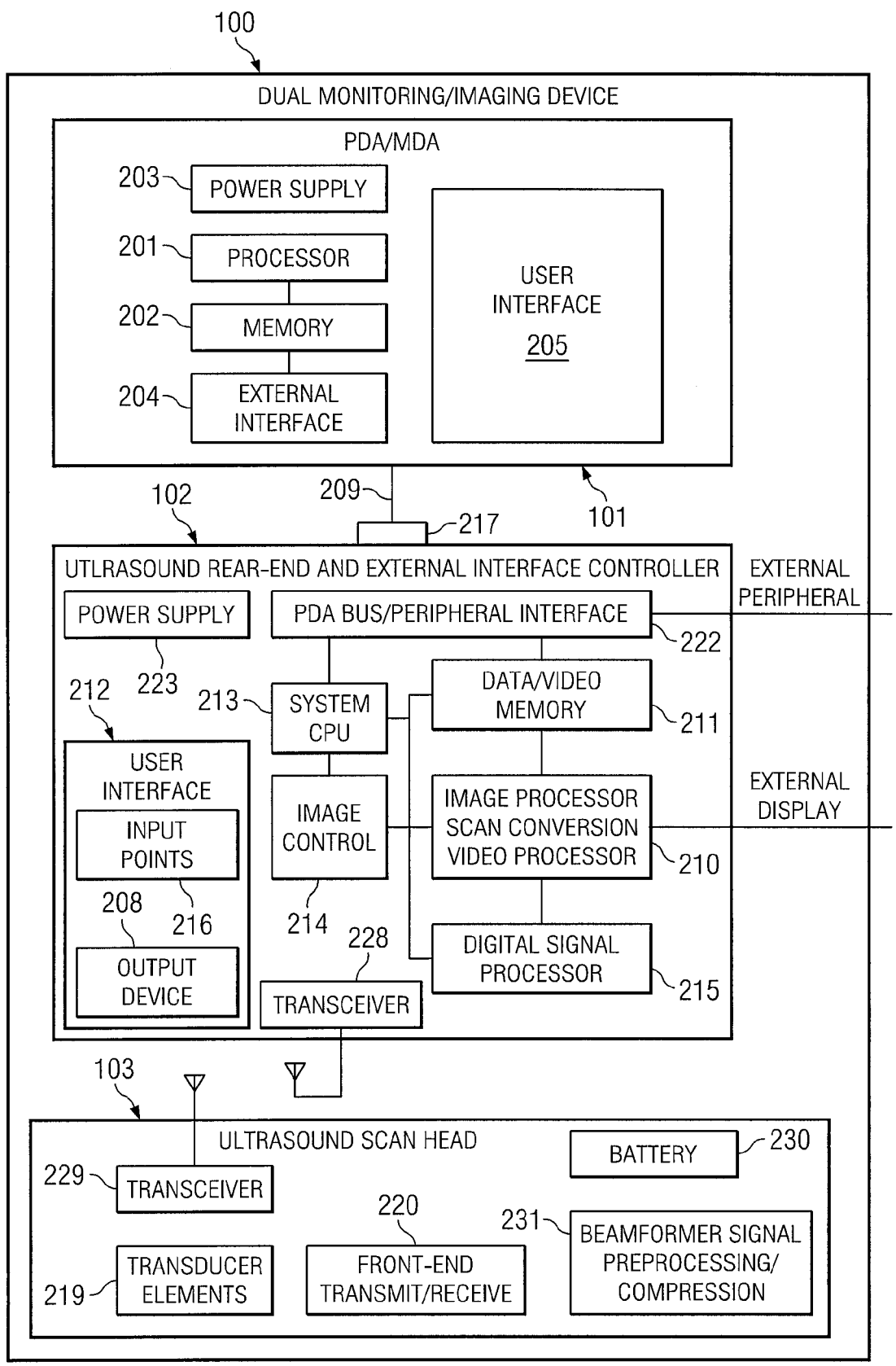
FIG. 2F depicts a block diagram illustrating an embodiment of the device of FIG. 1 wherein an external controller wirelessly communicates with a scan head including a signal preprocessing and compression beamformer.

Like FIG. 2E, FIG. 2F depicts a block diagram where scan head 103 is not physically attached to external controller 102 but communicates with external controller 102 via a wireless interconnect, such as UWB. However, scan head 103 of FIG. 2F includes beamformer 231 wherein digital signal preprocessing and compression may be performed in scan head 103 prior to transmission of signals to external controller 102. Signals preferably are acquired by scan head 103, processed and compressed by beamformer 231, and transmitted from transceiver 229 to transceiver 228 in a compressed format, allowing for more efficient bandwidth utilization.

FIGS. 3A-3D depict four different operational modes of one embodiment of PDA/MDA 101 identifying how output device or display 207 preferably may be configured based on the user's needs. It should be appreciated that different views may be desirable based on whether PDA/MDA 101 is being used by a medical technician performing the monitoring and/or imaging procedures or by a physician (remote expert) remotely monitoring a medical technician performing the procedures. The user determines which views are desired for output on display 207, as each of the views depicted in FIGS. 3A-3D are available to the user.

Figure 3A:
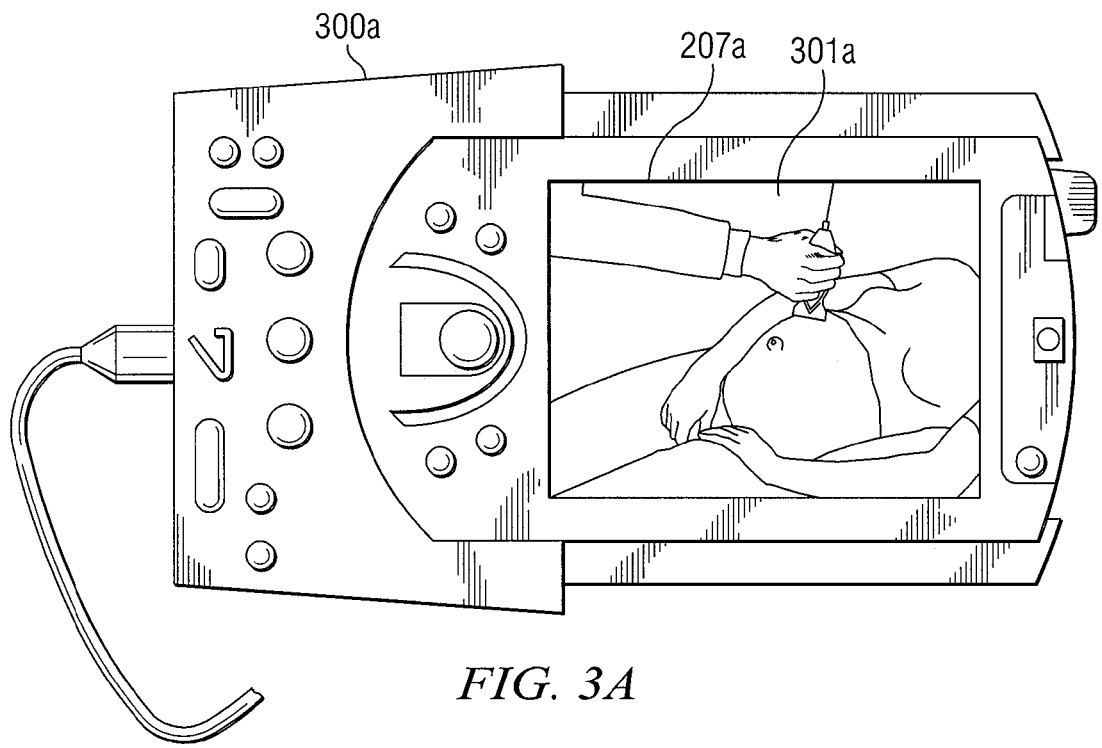
FIG. 3A depicts an embodiment of the unified device of FIG. 1 wherein the real-time video function is displayed.

Turning to FIG. 3A, in device 300a, a single image display 301a is shown on output device 207a, and in this case, real-time video feed may be captured (e.g., via a camera) and displayed on the screen. A physician may prefer this view in the situation where he/she is remotely monitoring a medical technician's actions in performing ultrasound imaging on a patient. The physician may view the positioning of the ultrasound scan head on the patient's body, allowing the physician to instruct the medical technician as to the proper positioning of the ultrasound scan head for the imaging procedure. This view also may be preferable when a medical technician walks away from a patient's room but desires to continue monitoring the vital signs of the patient.

Figure 3B:
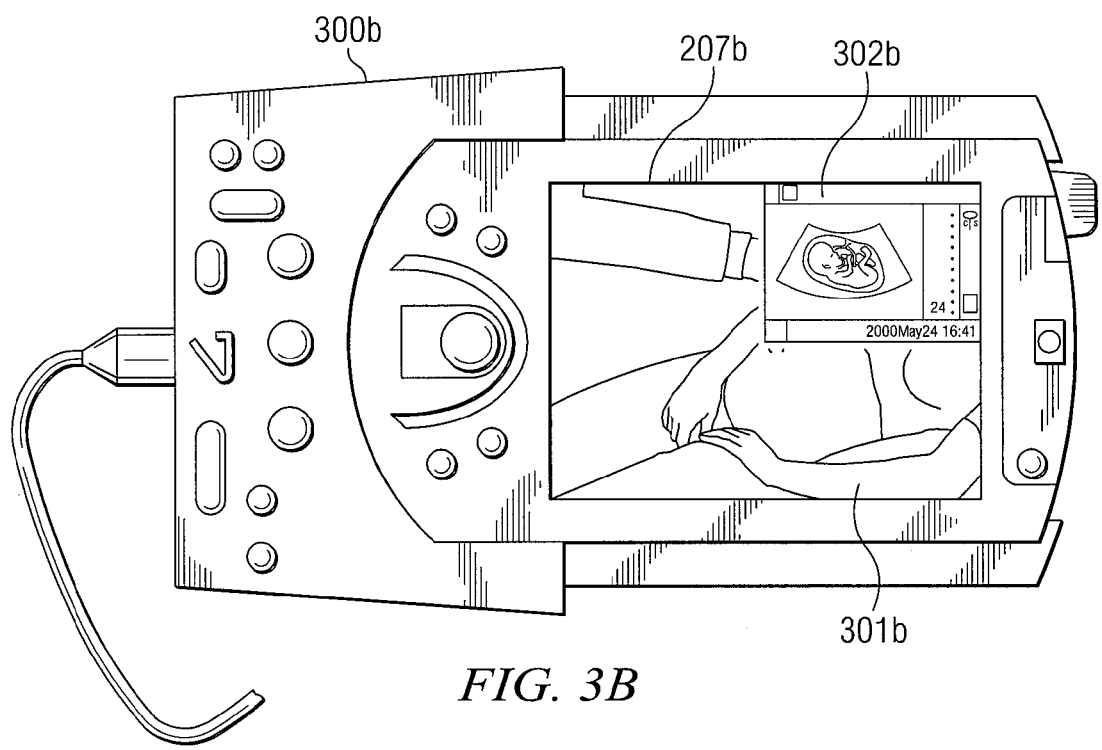
FIG. 3B depicts an embodiment of the unified device of FIG. 1 wherein both the real-time video function and the ultrasound imaging display function are displayed.

FIG. 3B depicts device 300b wherein a picture-in-picture display function is employed. In this scenario, two display windows 301b, 302b are shown on output device 207b. Display window 302b encompassing approximately one-fourth of display 207b displays the ultrasound image that has been processed after the medical technician has positioned the scan head on the patient's body. Display window 301b covers the remainder of output device 207b and provides real-time video streaming. In this embodiment, a remote expert may view how an ultrasound scan head is being positioned relative to the patient's body in display window 301b, and then refer to display window 302b to assess the images that result when the ultrasound scan head collects images.

Figure 3C:
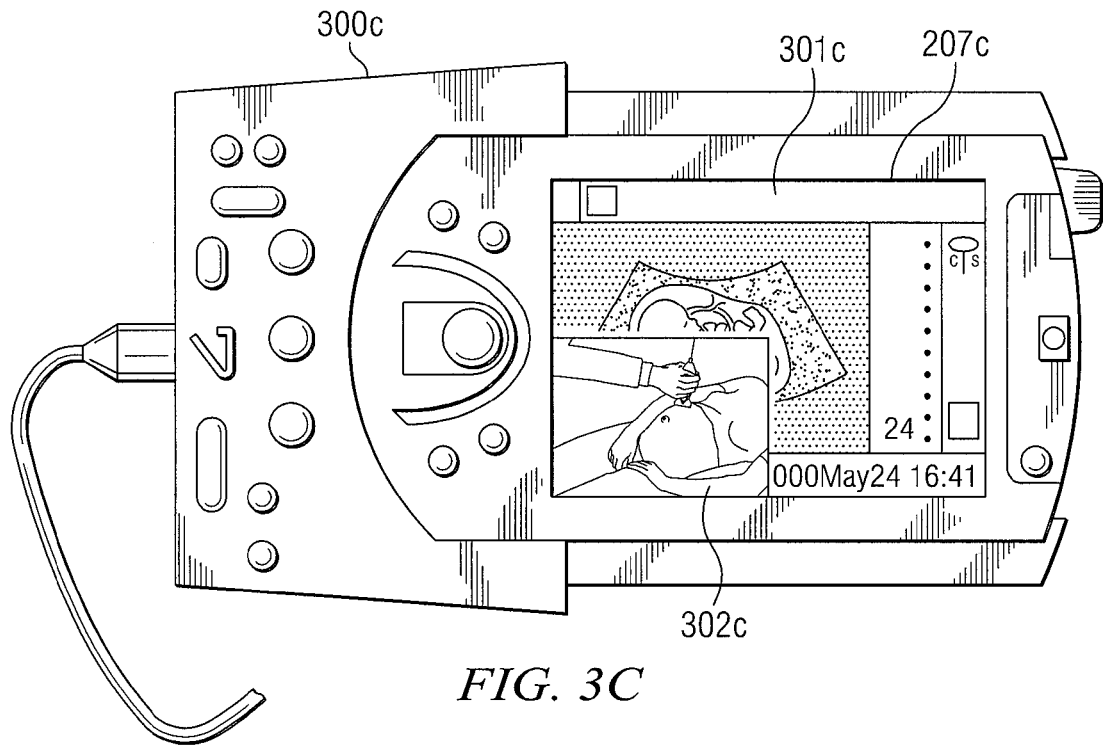
FIG. 3C depicts an embodiment of the unified device of FIG. 1 wherein both the real-time video function and the ultrasound imaging display function are displayed.

When a remote expert becomes comfortable with the positioning of a scan head relative to the patient's body, the remote expert may reverse the size and placement of the display windows of FIG. 3B. In FIG. 3C, the larger of the two display windows, display window 301c, shows the ultrasound image that has been processed after the medical technician acquires ultrasound images using the ultrasound scan head. The remote expert may prefer to continue reviewing the placement of the ultrasound scan head, and accordingly, approximately one-fourth of output device 207c includes display window 302c which provides a view with real-time video streaming showing how the scan head is placed on the patient's body for acquisition of ultrasound images.

Figure 3D:
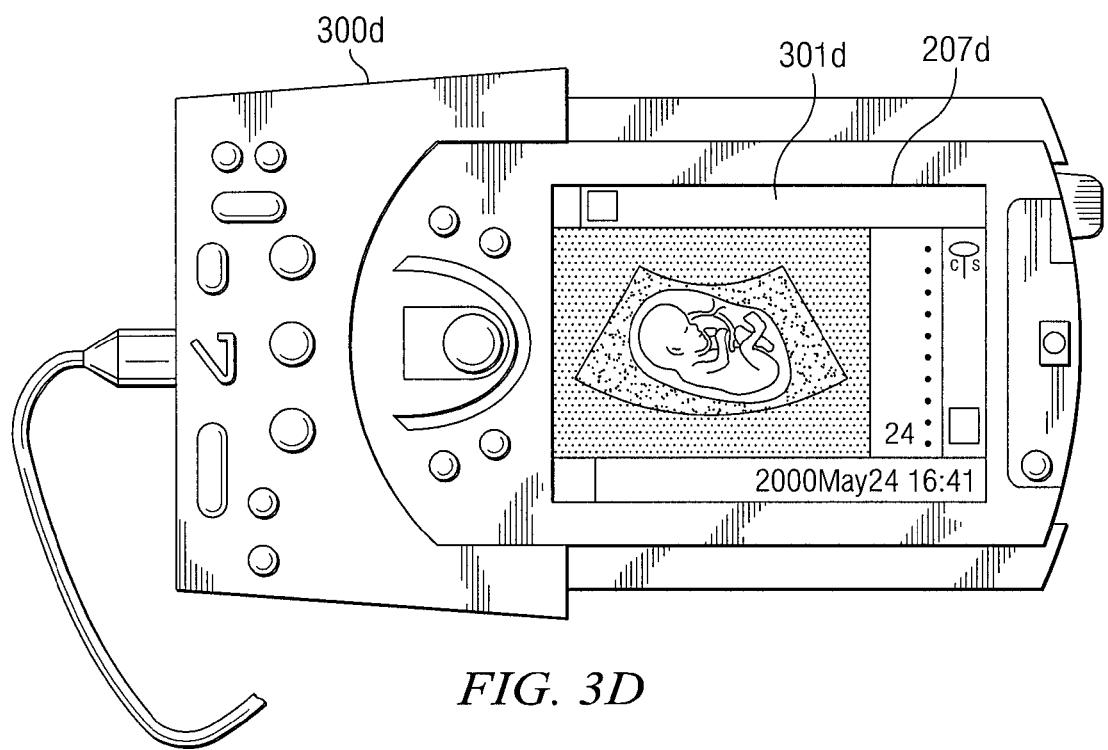
FIG. 3D depicts an embodiment of the unified device of FIG. 1 wherein the ultrasound imaging display function is displayed.

FIG. 3D depicts device 300d having a single display window 301d on output device 207d. In this embodiment, the display window shows the ultrasound image that has been acquired through use of an ultrasound scan head. This type of display may be preferable for a remote expert viewing the images that have been acquired by ultrasound, such as in the situation where the remote expert is monitoring ultrasound image acquisition to identify a particular characteristic. In other embodiments, a medical technician performing ultrasound image acquisition may prefer this type of display because he/she does not have a need to view real-time image video feed of the procedure since he/she is performing the procedure.

As has been shown in FIGS. 3A-3D, different options preferably are offered for configuring display windows on the display of a dual-mode handheld device, such as device 100. It should be appreciated, however, that the placement and sizing of the display windows are not fixed, and accordingly, the user may translate the smaller display window to a different corner of the display, for example. In further embodiments, the user may prefer a split-screen view, wherein the real-time video streaming display window and the imaging processing display window are similarly sized.

Figure 4:
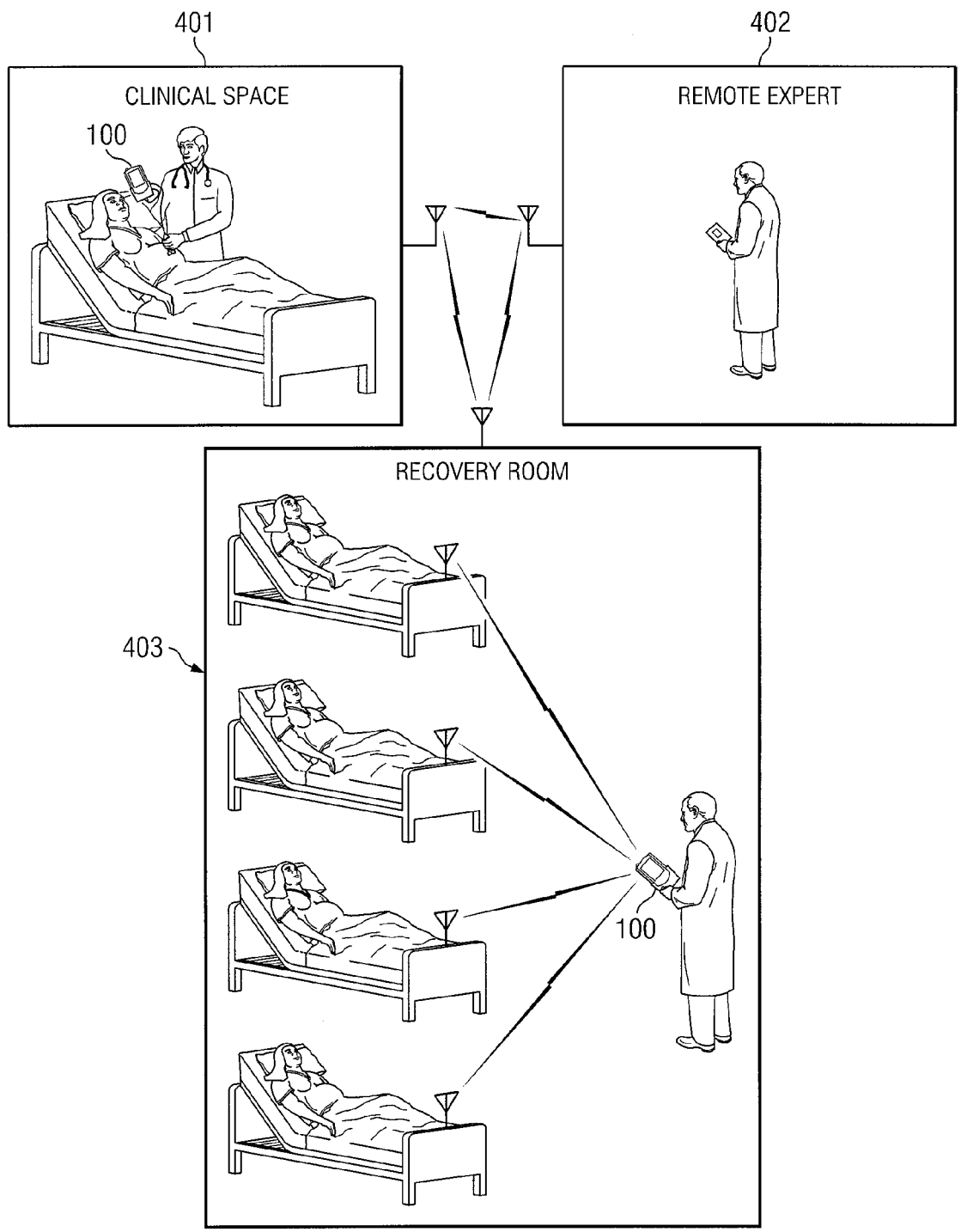
FIG. 4 is a system for using the device of FIG. 1 in a clinical space.

With the components and operation of the multi-function device 100 in mind, FIG. 4 depicts a clinical space, such as a hospital, utilizing device 100. In FIG. 4, a medical technician monitors and/or performs imaging procedures on a single patient in room 401 using device 100.

As a unified device, PDA/MDA 101 and external controller 102 of embodiments provide for UWB capability such that a high resolution ultrasound image may be transmitted to the PDA/MDA. For example, a medical technician using device 100 may leave room 401, walk down the hall and continue to monitor a single patient using the same bandwidth as discussed with respect to FIG. 2C. Further, even if an ultrasound image is not being transmitted, external controller 102 preferably has UWB capability so device 100 may monitor a number of patients simultaneously using the same bandwidth as discussed with respect to FIG. 2D.

In an embodiment of the present invention, if multiple patients were recovering in the same room, the medical technician or physician may use device 100 to monitor each of the patients in the room at the same time as shown in recovery room 403. According to one embodiment, small transmitters are connected to the beds of each patient to be monitored, and the transmitters are in contact with the monitoring probes, such as temperature or blood pressure probes, attached to the patient. Device 100 communicates with each of these transmitters associated with the patients in order to monitor the progress of each patient. However, it should be appreciated that in this scenario, the UWB capability is being split between a number of patients in order to monitor each of the patients simultaneously.

Additionally, wireless monitoring of a patient is conducted by attaching probes to the patient. These probes have wireless transmission capabilities such that PDA/MDA 101 of device 100 may display transmissions acquired from the probes received via external controller 102.

By incorporating UWB capability, improvement of the signal to noise ratio may be achieved by repetitive transmission. As an example, suppose the user wants to transmit 110 megabytes per second, and the UWB covers approximately 10 meters. If repetitive transmission is used, the user then could achieve 100 meters in the same bandwidth by applying a more repetitive type of spreading. The spread trunk uses longer time sequences to transmit the same information. Thus, the user can take advantage of the scalability of the UWB to support many short distance narrow band patients, meaning that more narrow band applications may be supported in a short distance, thus allowing the device to serve one narrow band application for a long distance. Further, the scalability also will support long distance narrow band applications.

The bandwidth available also may be effectively utilized in order to simultaneously perform a data transfer from scan head 103 to external controller 102. Similarly, the bandwidth may be used to stream video to PDA/MDA 101 attached to external controller 102 in order to obtain a more complete view of the patient's progress.

An embodiment of this system connects device 100 being used in room 401 to a remote expert in room 402. Again, a medical technician performs monitoring and imaging procedures using multi-function device 100 in surgical suite 401. Device 100 is preferably wirelessly linked to a communication device or display associated with a remote expert, such that the remote expert may monitor the actions of the medical technician in room 402. The remote expert preferably receives real-time video streaming as well as image display in room 402. It should be appreciated, however, that the remote expert does not need to remain in room 402 but may, for example, enter recovery room 403 while continuing to monitor ultrasound image acquisition that is being conducted with dual-function device 100 in room 401.

When device 100 is being used to transmit to a remote expert, typically a more ubiquitous, wireless wide area network is used. This network is typically a narrow band. Alternatively, transmission may occur through a local area network. In another embodiment, transmission may be achieved using the Internet. Many different pathways are available to transmit from the device to the remote expert, provided that the channel, a wireless or wired link, is available. Thus, multifunction device 100 may be connected to wireless radio in order to make information from room 401 available to the remote expert on his/her device in remote location 402. In order to make this remote monitoring possible, CMOS radio and extender implementations may preferably be utilized, although other implementations may be provided depending on the location of the remote expert relative to the surgical suite where monitoring and image acquisition are being performed.

Figure 5:
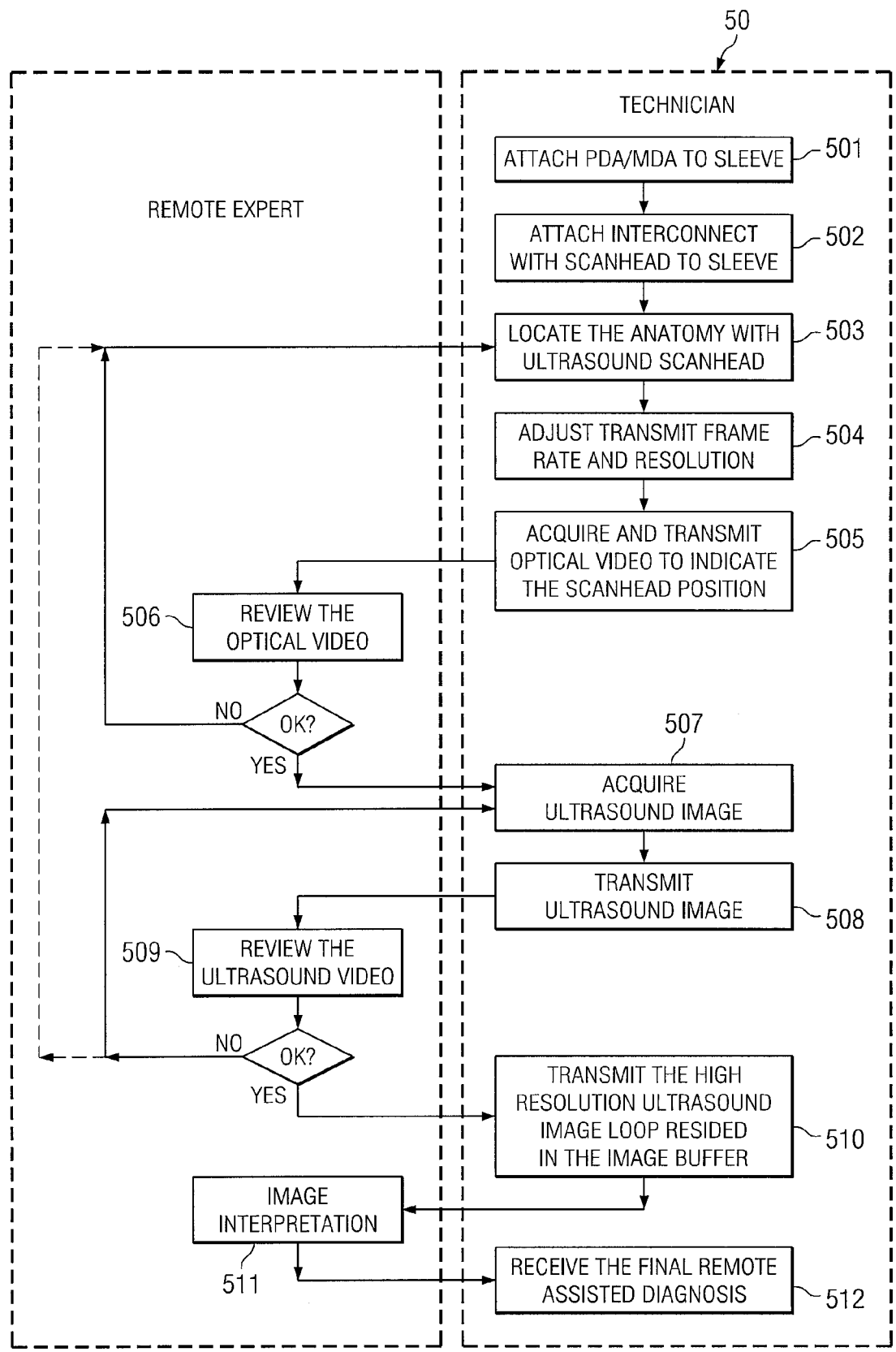
FIG. 5 is a method for using the device of FIG. 1 in a clinical space.

FIG. 5 depicts a block diagram illustrating how dual-function device 100 may be used to provide both real-time video stream monitoring as well as image acquisition in a clinical space. Further, FIG. 5 depicts how a technician may use dual-function device 100 in one area of a hospital, for example, and communicate video and/or images to a remote expert. It follows that the steps depicted in FIG. 5 have been identified as occurring on the remote expert side or on the technician side accordingly.

In step 501, the medical technician releasably attaches PDA/MDA 101 to external controller 102. In step 502, the medical technician attaches external controller 102 to scan head 103 via interconnect 104, such as a cable or antenna. Although the method is being described as including a step for attaching external controller 102 to scan head 103, it should be appreciated that interconnect 104 and scan head 102 may already been attached to external controller 102 at the time that the medical technician enters the clinical area. It also should be appreciated that external controller 102 and scan head 103 may not be physically attached, as has been described with respect to FIGS. 2E and 2F.

In step 503, the medical technician locates the portion of the patient's anatomy that is to be monitored and/or imaged using scan head 103. In step 504, the medical technician, using device 100 may adjust the transmit frame rate and resolution to adapt to the available radio bandwidth.

When image acquisition is to be performed, the medical technician inserts an optical acquisition unit, e.g., a video camera or other imaging device, into PDA/MDA 101. The medical technician acquires and transmits optical video to indicate the position of scan head 103 in step 505. Once this optical acquisition unit has been asserted, the medical technician approaches the patient and points device 100 at the patient in order to obtain a video image of the patient on display 207. Accordingly, the medical technician may view the patient, using real-time video streaming, in order to look at the patient's face, the positioning of the patient's body, and other vital signs. In another dual-mode operation using device 100, probes or sensors are connected to a patient and communicate with device 100 via a transmitter affixed to the patient's bed. For example, information about a patient's vital signs may be obtained by communication between the transmitter affixed to a patient's bed and the optical acquisition unit that has been inserted in device 100. This optical acquisition unit acquires the anatomy and allows transfer of the acquired images in real-time to both display 207 of PDA/MDA 100 or to a remote expert.

This optical video may be transmitted to a remote expert, and in step 506, the remote expert reviews the optical video transmitted by the medical technician. If the remote expert approves of the positioning of scan head 103, he/she will send instructions to the medical technician to acquire an ultrasound image, and the medical technician will acquire the image in step 507. However, if the remote expert does not agree with the positioning of scan head 103, instructions will be sent back to the medical technician. Accordingly, the medical technician may repeat steps 503-505 until proper positioning of scan head 103 has been achieved.

When an ultrasound image has been acquired by the medical technician, in step 508, the acquired image may be transmitted back to the remote expert. The remote expert reviews ultrasound video in step 509. If the remote expert approves of the images that he/she receives, then in step 510, the medical technician transmits a high resolution ultrasound image loop that has resided in the image buffer to the remote expert.

Accordingly, the remote expert may assess the acquired images in order to identify changes that may be made to the imaging and/or monitoring procedure. If, however, the remote expert does not approve of the video feed, the remote expert may have two options. The remote expert may direct the medical technician to return to step 507 in order to acquire another image and transmit that image to the remote expert again in step 508 for review. Alternatively, the remote expert may determine at this stage that the medical technician should return to step 503 to locate the patient's anatomy for an additional time in order that the remote expert may review the scan head position and assess how the positioning affects the image that was acquired in step 507.

When the remote expert acknowledges satisfactory acquisition, the stored high resolution image loop in the system memory may now be forwarded to the remote expert for review. Transmitting a high resolution image sequence may use substantially more bandwidth, and accordingly more time or an augmented radio bandwidth may be used. However, this may not be problematic in that hand-eye coordination is only needed during image acquisition using "real-time" video streaming. Thus, when the image acquisition process is completed, transfer of images with additional latency may be appropriate. When the remote expert receives the high resolution ultrasound image loop transmitted in step 510, the remote expert may engage in image interpretation in step 511. In step 512, the medical technician receives the final remote assisted diagnosis of the patient.

In an alternative embodiment, a stand alone handheld ultrasound device may display the ultrasound image on display 207 of PDA/MDA 101. Accordingly, the medical technician may not communicate with a remote expert if no assistance is required. As an example, a physician may use device 100 to monitor patients recovering in the same room and then to perform imaging procedures using device 100 as needed. In this embodiment, a physician is utilizing device 100 and may not need to transmit real-time data to another physician.

It should be appreciated that the medical technician, physician and/or remote expert viewing monitoring and imaging information from multiple sources on device 100 may find, for example, that the ultrasound image is a lower quality image than would be typically displayed. However, this change in quality is due to accommodating both the real-time video stream monitoring and image display on the medical technician's device, such as device 100. In order to adequately or more efficiently use the bandwidth available for optical acquisition, the image quality may be degraded because device 100 may contain a large amount of information, including optical acquisition information as well as ultrasound information.

When ultrasound images are displayed on device 100, the medical technician may choose to store the images on his/her device. However, it should be appreciated that these ultrasound images typically are acquired in real-time. When the images are transmitted to the remote expert, this transmission is typically performed by degrading images to be sent via radio transmission, for example. Higher quality images may be sent via radio transmission; however, transmission may occur using more bandwidth or by taking a longer period of time to transfer using the same bandwidth. Images are fed into the memory of the device continuously, and accordingly, image acquisition employs a first-in, first-out methodology. As an example, a high resolution image frame of 512×512 pixels is sequentially stored into the image buffer. Provided that there is not sufficient bandwidth to transfer such a high resolution image in real time, the image may be filtered and decimated into 256×256 pixel resolution. By doing so, bandwidth is preferably reduced by a factor of 4 as compared to the bandwidth typically needed for transferring an image frame of 512×512 pixels. A reduction by a factor of 16 may be achieved if the image frame is filtered and then decimated to 128×128 pixels. Methods for trading-off resolution and/or frame rates to available bandwidth are implemented in software for image applications that demand "real-time" video streaming.

Although device 100 has been described with respect to integrating the PDA/MDA with a sleeve equipped for ultrasound diagnostic applications, PDA/MDA 101 and external controller 102 may be programmed for other applications, depending on the preferences of the user or the requirements of the facility in which device 100 is being used.

It should be appreciated that as PDA/MDA technology changes, such as when a PDA manufacturer designs an upgrade, typically no change in the interface of external controller 102 is required. Accordingly, an upgraded PDA/MDA 101 may be incorporated into the multi-function device easily and at a low cost.

Although the interconnects have been described as being wireline or wireless radios of various types, it should be appreciated that a single super broad band wireless radio may be implemented to replace these interconnects. Accordingly, the system architecture may be simplified, for example, into acquisition sensor/radio, user interface/radio, processing server/radio, and display/radio or different combination of modules/radio.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A medical system supporting imaging and monitoring applications said system comprising:

an ultrasound adapter for collecting and processing data with respect to a patient wherein said data includes imaging and monitoring information;

a scan head in communication with said ultrasound adapter for acquiring said imaging information and transferring said imaging information to said ultrasound adapter;

at least one physiological sensor in communication with said ultrasound adapter for acquiring said monitoring information and transferring said monitoring information to said ultrasound adapter; and a general purpose computer in communication with said ultrasound adapter, wherein said ultrasound adapter releasably receives said general purpose computer and said general purpose computer displays said data collected and processed by said ultrasound adapter, and wherein said system simultaneously performs said imaging and monitoring applications on a patient.

2. The system of claim 1 wherein said system is portable.

3. The system of claim 1 wherein said system performs monitoring of more than one patient simultaneously.

4. The system of claim 1 said system having ultra wide band capability wherein said system monitors more than one patient simultaneously.

5. The system of claim 1 said system having ultra wide band capability wherein a high resolution image of a patient obtained by said ultrasound adapter is displayed on said general purpose computer.

6. The system of claim 1 wherein said system monitors a patient in a location remote from the patient.

7. The system of claim 1 wherein said system acquires monitoring and imaging information for transmittal to a third party in a remote location.

8. The system of claim 7 wherein a wide area network transmits said monitoring and imaging information from said system to said third party.

9. The system of claim 1 further comprising an interconnect between said scan head and said ultrasound adapter to facilitate communication and transfer of information between said scan head and said ultrasound adapter.

10. The system of claim 9 wherein said interconnect is a wireless connection.

11. The system of claim 9 wherein said interconnect is a hardwire connection.

12. The system of claim 9 wherein said interconnect is a super broad band wireless radio.

13. The system of claim 1 wherein said general purpose computer is a personal digital assistant (PDA).

14. The system of claim 1 wherein said general purpose computer further comprises:

an external interface providing connectivity of said general purpose computer with remote systems.

15. The system of claim 14 wherein said external interface attaches to an external monitor for display of said data collected by said ultrasound adapter.

16. The system of claim 1 said general purpose computer having a user interface comprising:

physical input points; and
a display.

17. The system of claim 16 wherein said user interface displays video feed collected by said system.

18. The system of claim 16 wherein said user interface displays images acquired by said scan head.

19. The system of claim 16 wherein said display permits simultaneous viewing of video feed collected by said system and images acquired by said scan head.

20. The system of claim 19 wherein said display is picture-in-picture.

21. The system of claim 19 wherein said display is a split-screen view.

22. The system of claim 1 wherein said general purpose computer is an external monitor.

23. The system of claim 1 wherein said general purpose computer is wirelessly connected to said ultrasound adapter and receives signals processed by said ultrasound adapter.

24. A method for performing imaging and monitoring applications, said method comprising:

electrically coupling a PDA/MDA to an external controller;

placing a scan head in communication with said external controller;

integrating an optical acquisition unit into said PDA/MDA;

under control of said PDA/MDA, acquiring and transmitting optical video of a patient;

under control of said scan head, acquiring signals to be processed into images of said patient;

attaching at least one robe to said patient wherein said at least one probe communicates with said external controller to provide monitoring information; and under control of said external controller, converting said signals into images, processing said monitoring information and transferring said images and said monitoring information from said external controller to said PDA/MDA, wherein said PDA/MDA simultaneously displays at least two of said optical video, said monitoring information and said images.

25. The method of claim 24 wherein said PDA/MDA selectively displays said optical video, said monitoring information and said images.

26. The method of claim 24 wherein a user of said PDA/MDA selects what is to be displayed on said PDA/MDA.

27. The method of claim 24 wherein a user, using said PDA/MDA, transmits said optical video, said monitoring information and said images to a third party in a remote location.

28. The method of claim 24 wherein said PDA/MDA displays said optical video, said monitoring information and said images in a picture-in-picture format.

29. The method of claim 24 wherein said at least one probe communicates with said external controller via a transmitter attached to said patient's bed.

30. The method of claim 24 wherein said external controller monitors said patient in a location remote from said patient.

31. A portable medical device comprising:

an external controller in the form of a sleeve receiving a PDA via an output device forming a unified device for processing and displaying monitoring and ultrasound imaging data;

a scan head in communication with said external controller wherein said scan head acquires and communicates ultrasound imaging data to said external controller;

at least one physiological sensor in communication with said external controller for acquiring said monitoring data and transferring said monitoring data to said external controller; and wherein said external controller processes data collected by said scan head and said at least one sensor and transfers said data to said PDA for display.

32. The portable medical device of claim 31 wherein said external controller is a sleeve.

33. The portable medical device of claim 31 wherein said external controller is a docking station.

34. The portable medical device of claim 31 said external controller comprising:

at least one processor;
a storage device;

a user interface;
a peripheral interface.

35. The portable medical device of claim 34 said at least one processor comprising:
    a digital signal processor filtering signals received from said scan head; and
    an image processor wherein said image processor receives said signals from said digital signal processor and performs scan conversion.

36. The portable medical device of claim 31 said data further comprising real-time video feed and images acquired from said scan head.

37. The portable medical device of claim 31 wherein an external add on card is inserted into a peripheral interface of said external controller.

38. The portable medical device of claim 37 wherein said external add on card processes signals received from said scan head.

39. The portable medical device of claim 31 wherein said external controller is electrically attached to an external monitor.

40. The portable medical device of claim 39 wherein said external controller and said external monitor are attached via a video port.

41. The portable medical device of claim 31 wherein said data is transmitted to a remote third party for viewing.

42. The portable medical device of claim 41 wherein said data is transmitted via a wireless wide area network.

43. The portable medical device of claim 41 wherein said data is transmitted via a local area network.

44. A method for performing dual-mode ultrasound imaging and video applications, said method comprising:
    electrically coupling a general purpose computer to an ultrasound adapter via a releasable communication link;
    placing a scan head in communication with said ultrasound adapter;
    pointing said general purpose computer coupled to said ultrasound adapter in the direction of at least one patient to acquire video of said at least one patient;
    under control of said scan head, acquiring signals to be processed into ultrasound images of said patient; and
    under control of said ultrasound adapter, converting said signals into ultrasound images and transferring said ultrasound images and said video for viewing on said general purpose computer,
    wherein said dual-mode imaging and video applications are simultaneously performed on a patient.

45. The method of claim 44 wherein said general purpose computer selectively displays said video and said ultrasound images.

46. The method of claim 44 wherein said general purpose computer simultaneously displays said video and said ultrasound images.

47. The method of claim 44 wherein said video is acquired from more than one patient in the same location.

48. The method of claim 44 wherein said video and said ultrasound images are transmitted to a third party in a remote location.

49. The method of claim 44 wherein said ultrasound adapter acquires video from at least one patient in a location remote from said at least one patient.

* * * * *

UNITED STATES PATENT AND TRADEMARK OFFICE
CERTIFICATE OF CORRECTION

| | |
|---|---|
| PATENT NO. | : 7,549,961 B1 |
| APPLICATION NO. | : 10/903848 |
| DATED | : June 23, 2009 |
| INVENTOR(S) | : Juinjet Hwang |

It is certified that error appears in the above-identified patent and that said Letters Patent is hereby corrected as shown below:

Column 16, Claim 24, Line 17, delete the portion of text reading "robe" and replace with --probe--.

Signed and Sealed this

Twenty-fifth Day of August, 2009

David J. Kappos
*Director of the United States Patent and Trademark Office*